| (12) United States Patent<br>Swain | (10) Patent No.: US 8,690,902 B2<br>(45) Date of Patent: Apr. 8, 2014 |
|---|---|
| (54) METHOD OF ENLARGING AN ANASTOMOSIS FISTULA INTO A LARGER ANASTOMOSIS | (56) References Cited<br><br>U.S. PATENT DOCUMENTS<br><br>6,843,794 B2 1/2005 Sixto, Jr. et al.<br>7,357,806 B2 4/2008 Rivera et al.<br>2006/0011698 A1* 1/2006 Okada et al. ............... 227/175.1<br>2008/0078802 A1* 4/2008 Hess et al. ............... 227/175.1<br><br>* cited by examiner<br><br>*Primary Examiner* — Corrine M McDermott<br>*Assistant Examiner* — Son Dang<br>(74) *Attorney, Agent, or Firm* — Nutter McClennen & Fish LLP |
| (75) Inventor: Christopher P. Swain, London (GB) | |
| (73) Assignee: Ethicon Endo-Surgery, Inc., Cincinnati, OH (US) | |
| (*) Notice: Subject to any disclaimer, the term of this patent is extended or adjusted under 35 U.S.C. 154(b) by 549 days. | |
| (21) Appl. No.: 12/939,632 | |
| (22) Filed: Nov. 4, 2010 | |
| (65) Prior Publication Data<br><br>US 2012/0116426 A1 May 10, 2012 | (57) ABSTRACT<br><br>Methods and devices are provided for enlarging an anastomosis fistula. In general, a surgical clip is applied to tissue surrounding a strictured anastomosis. The clip will exert a pressure on the engaged tissue that causes ischemic necrosis, and as a result the necrotic tissue and the clip will slough off, leaving an anastomosis with a larger diameter fistula.<br><br>20 Claims, 13 Drawing Sheets |
| (51) Int. Cl.<br>*A61B 17/08* (2006.01)<br>(52) U.S. Cl.<br>USPC ............... 606/154; 606/153; 227/175.1<br>(58) Field of Classification Search<br>None<br>See application file for complete search history. | |

METHOD OF ENLARGING AN ANASTOMOSIS FISTULA INTO A LARGER ANASTOMOSIS

FIELD

The present invention relates to methods for performing surgical procedures, and in particular to methods and devices for enlarging strictured anastomosis fistulae.

BACKGROUND

An anastomosis is the joining of luminal structures within the body by way of collateral channels when the natural channels are blocked. One common example is a colonic anastomosis in which two portions of the colon are joined together. Creating an anastomosis is a critical step in many surgical procedures, including those that address diseases as wide-ranging as cancer and obesity. For example, a gastrojejunostomy anastomosis may be created between the stomach and the jejunum to treat blockages in the duodenum or for malabsorption, e.g., gastric bypass surgery. An entero-enteral anastomosis may be created for jejuno-jeunal bariatric purposes, a colon to ileum anastomosis may be created for bypassing colorectal cancer, and a biliary duodenal anastomosis may be created between the bile duct and the duodenum above a malignant or benign obstruction in the bile duct.

An anastomosis may be created using open surgical procedures requiring the patient to be placed under general anesthesia, or using endoscopic or laparoscopic procedures that are much less invasive and often do not require general anesthesia. In addition to traditional cutting and stapling or suturing procedures, compression or suture-less techniques can also be used to create an anastomosis. A compression anastomosis is formed by necrotic ischemia caused by the occlusion of the blood supply to the tissue. Compression is applied to the tissue using one or more masses to sandwich the tissue in the target area. One compression anastomosis technique employs a compression button that erodes through the bowel wall over several days because of ischemic necrosis resulting in a leak-free anastomosis. Another suture-less compression anastomosis technique employs a bio-fragmentable ring to create an anastomosis in the bowel.

Other anastomoses may be created using flexible endoscopy techniques employing spring compression buttons. Flexible endoscopy anastomosis techniques may employ ultrasonography techniques when access is limited to a single endoscopic lumen. Magnets also have been used to form compression anastomoses when access is possible to both transgastric lumens or by passing a device through the jejunum. Magnetic compression gastroenteric anastomoses may be performed by introducing magnets perorally with endoscopic and fluoroscopic guidance and mated across the gastric and jejunal walls. Compression anastomoses may be formed between bile ducts using magnets following duct stenosis in liver transplant patients.

In many cases, the anastomosis fistula becomes strictured, or narrowed, over a period of time. This may be due to the method used to create the anastomosis fistula, e.g., using small magnets results in a small fistula between body lumens, or may be the result of the natural healing behavior of the body, e.g., tissue building up around the anastomosis fistula. In some cases, the strictured anastomosis is not large enough to effectively pass contents between the two body lumens. As a result, there is a need for methods of enlarging a strictured anastomosis fistula to more effectively pass contents between the two body lumens. Various methods exist in the prior art, including the use of balloons or stents to dilate and retain the size of an anastomosis fistula. However, these methods can be complicated and risk tearing the fistula. Accordingly, there remains a need for improved methods for enlarging an anastomosis.

SUMMARY

The present invention generally provides methods for enlarging an anastomosis fistula. In one embodiment, an endoscope is advanced through a first lumen to a site of a strictured anastomosis formed between the first lumen and a second lumen. A first leg of a clip is then positioned in the second lumen and a second leg of the clip is positioned in the first lumen. The first and second legs of the clip are then closed to apply a pressure to tissue surrounding the strictured anastomosis that is sufficient to induce ischemic necrosis in the compressed tissue. After a period of time, the necrotic tissue and clip will slough off and pass through one of the first and second lumens, resulting in a larger diameter anastomosis fistula. In an exemplary embodiment, the first lumen is the stomach and the second lumen is the small intestine.

Various techniques can be used to deliver the clip. In one embodiment, the method can include, prior to positioning, using at least one guidewire to advance the clip to the site of the strictured anastomosis. For example, the first leg of the clip can be advanced along a first guidewire extending through the endoscope, and the second leg of the clip can be advanced along a second guidewire extending through the endoscope. Prior to advancing the clip, the first guidewire can be passed through the endoscope and the strictured anastomosis to position a distal end of the first guidewire in the second lumen, and the second guidewire can be passed through the endoscope to position a distal end of the second guidewire in the first lumen. In another embodiment, the clip can be delivered by advancing a flexible clip applier through the endoscope to position the clip adjacent to the strictured anastomosis.

The method can be used with various clips. In one embodiment, the clip can have first and second legs that are biased to a closed position. The first and second legs can be closed by releasing the clip from a delivery device. The clip can also have ball-shaped or curled ends to prevent puncturing of the lumen walls. In another embodiment, the clip can be a closed by the application of a deforming force from a delivery device.

In another embodiment, an endoscope is advanced through a first body lumen to position a distal end of the endoscope adjacent to a strictured anastomosis formed between the first body lumen and a second body lumen. A clip is then applied to the strictured anastomosis such that the first and second terminal ends of the clip apply a pressure sufficient to induce ischemic necrosis to cause the clip and surrounding tissue to slough off and thereby increase a diameter of the anastomosis fistula. The clip can have various configurations and it can be delivered using various techniques, as explained above.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is directed toward methods and devices for enlarging an anastomosis fistula. In general, a surgical clip is applied endoscopically or laparoscopically to tissue surrounding a strictured anastomosis. The clip will exert a pressure on the engaged tissue that will cause ischemic necrosis, and as a result the necrotic tissue and the clip will slough off, leaving an anastomosis with a larger diameter fistula. The clip can also stimulate a healing response in surrounding tissue due to increased blood flow, thus facilitating better fusion between the two anastomosed body lumens.

Figure 1:
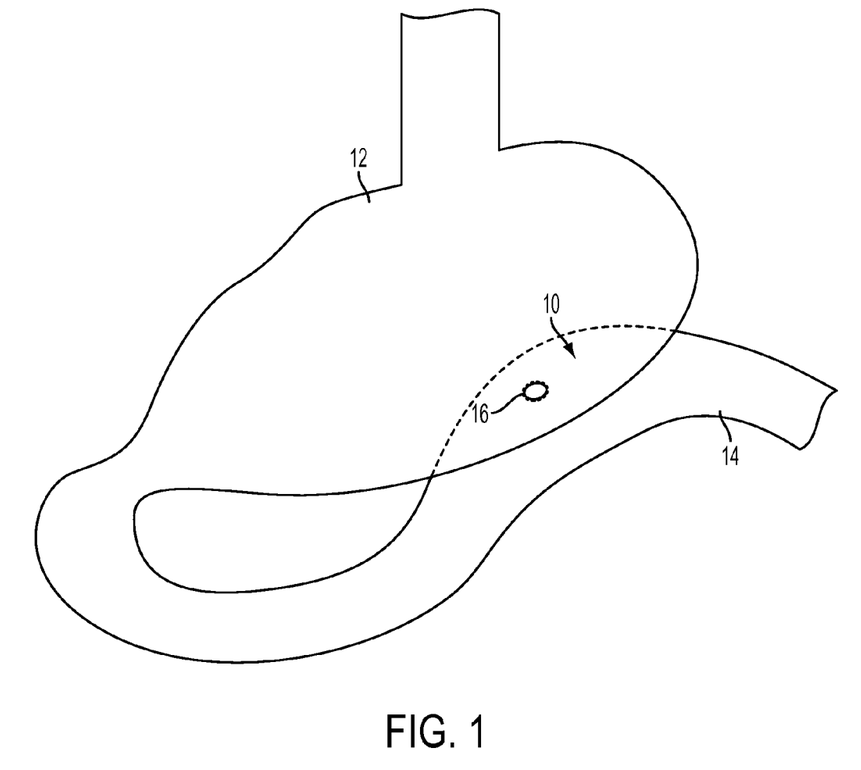
FIG. 1 is a front perspective view of an exemplary side-to-side anastomosis formed between a stomach and a small intestine.
Figure 2:
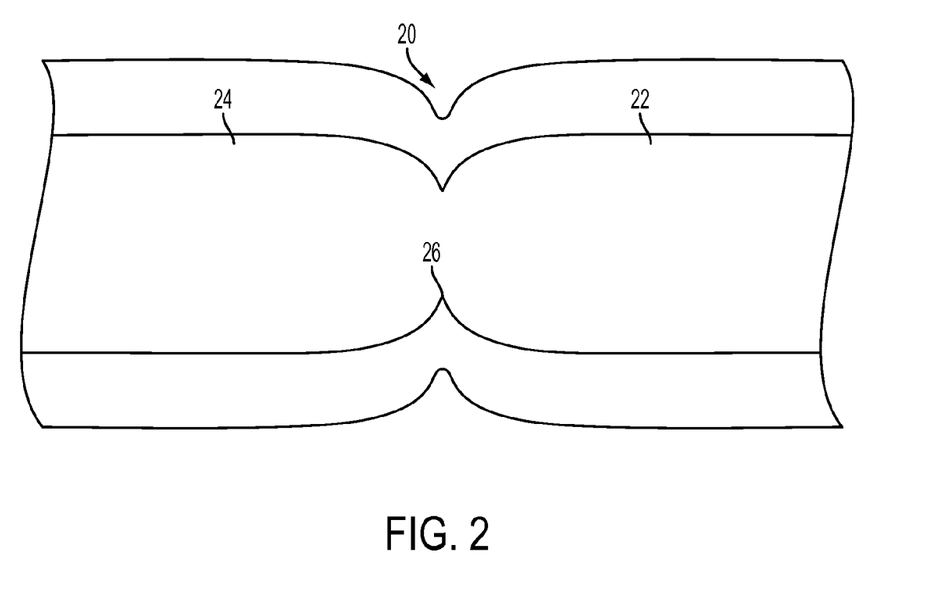
FIG. 2 is a side perspective view of an exemplary end-to-end anastomosis formed between two sections of a small intestine.

The method can be used to treat any anastomosis, i.e., any connection between two normally separate structures, such as the esophagus, stomach, small intestine, large intestine, colon, bile ducts, or pancreas. The anastomosis can be an end-to-end anastomosis formed by joining the two ends of two lumens together, a side-to-side anastomosis formed by joining an end of a body lumen to a side of a body lumen, or an end-to-side anastomosis formed by joining an end of a body lumen to a side of a body lumen. FIG. 1 depicts a side-to-side anastomosis 10 formed between the side walls of the stomach and small intestine. The anastomosis is defined by the presence of a first lumen 12 (the stomach), a second lumen 14 (the small intestine), and a fistula 16, or opening, that permits communication between the two. FIG. 2 illustrates an example of an end-to-end anastomosis 20 formed after, for example, resection of a portion of the small intestine. The anastomosis features a first lumen 22 (the first portion of the small intestine), a second lumen 24 (the second portion of the small intestine), and a fistula 26 permitting communication between the two. To join the two lumens together, surgeons utilize any of several mechanical fastening methods known in the art. Circular staplers are very commonly used to join the walls of the two lumens together.

The surgical creation of an anastomosis can leave a strictured, or narrowed, anastomosis fistula. FIGS. 1 and 2 illustrate strictured anastomosis fistulae, where the fistula has a smaller inner diameter than either of the two lumens. The anastomosis pictured in FIG. 2 illustrates a collapsed area of tissue surrounding the fistula. In some cases, an anastomosis fistula is so narrow that it cannot pass contents through the two lumens effectively. In such cases, it is desirable to extend the fistula to permit larger volumes of material to pass between the lumens.

As indicated above, a strictured anastomosis fistula can be enlarged by causing a portion of the tissue surrounding the fistula to undergo necrosis and slough off, resulting in a larger diameter fistula. To induce necrosis, a clip can be applied to the tissue surrounding the fistula and it can exert a pressure on the tissue. The clip can have a variety of configurations, and various surgical clips known in the art can be used. A person skilled in the art will appreciate that the term "clip" is used herein to refer to any device or implant that can engage tissue, including staples, crimps, and other similar structures known in the art. In general, the clip is preferably formed from a biocompatible material, and is either deformable to allow the clip to be compressed or bent into a closed configuration, is elastic and biased to one of an open or a closed configuration, or is held in a closed position by a retaining member. The size of the clip can also vary, and the particular size can depend on the size of the fistula, as well as the desired amount of expansion. In an exemplary embodiment, the clip has a size sufficient to induce ischemic necrosis thereby increasing a size of the anastomosis fistula. Preferred clips are in the size range of about 0.5 to 0.75 inches in length. For use in gastric anastomoses, preferred clips are in the size range of about 0.75 to 1.0 inches in length.

Figure 3A:
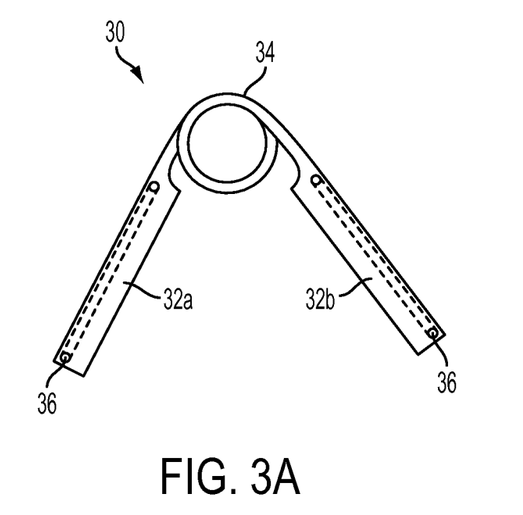
FIG. 3A is a front perspective view of one embodiment of a clip, shown in an open position, and effective to induce ischemic necrosis in tissue surrounding an anastomosis fistula.
Figure 3B:
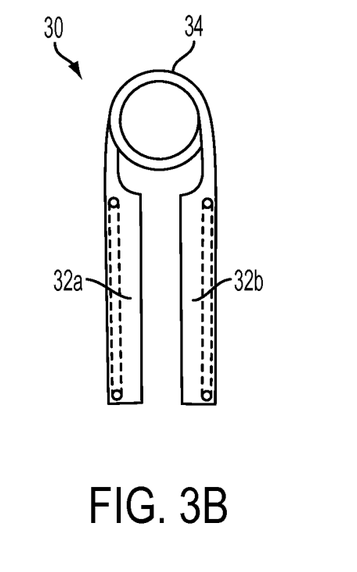
FIG. 3B is a front perspective view of the clip in FIG. 3A, shown in a closed position.

FIG. 3 illustrates one embodiment of a clip 30 for use in enlarging an anastomosis. As shown, the clip 30 generally has first and second legs 32a, 32b that are connected to one another at a first end. The legs 32a, 32b are movable between an open configuration, as shown in FIG. 3A, and a closed configuration, as shown in FIG. 3B. The clip 30 can be moved from the open position to the closed position by deforming the legs 32a, 32b toward one another, or in an exemplary embodiment, as shown, the legs 32a, 32b can be biased to the closed position. The clip 30 can be formed from a shape memory material, such as nitinol, and/or it can include a biasing element, such as a spring 34, for biasing the clip 30 to the closed position. In the illustrated embodiment, the spring 34 is in the form of a coil spring coupled between the first and second legs 32a, 32b. In use, the legs 32a, 32b can be held in the open position, and then released to allow the legs 32a, 32b to move to the closed position and to apply a pressure to the tissue. In an exemplary embodiment, the clip's biasing element is sufficiently strong to impart the necessary pressure on the tissue directly between the two legs to induce ischemic necrosis. The biasing element can also be effective to apply a constant pressure, and/or to apply a gradient pressure such that the greatest amount of pressure is exerted on tissue directly between the legs 32a, 32b of the clip 30, and a decreasing amount of pressure is exerted on tissue surrounding and more removed from the clip 30. After time, the compressed tissue undergoes necrosis due to ischemia, or loss of blood supply, and falls away from the fistula. The stress from the clip 30 can also stimulate a healing response in surrounding tissue not deprived of blood supply, promoting fusion of the surrounding tissue from each lumen.

As further shown in FIGS. 3A and 3B, the clip 30 can also include a lumen 36 extending longitudinally through one or both legs 32a, 32b for receiving a guidewire that can be used to direct the clip 30 to a surgical site. One or two guidewires can be used to position the clip 30 relative to the tissue surrounding the anastomosis fistula, as described further below.

Figure 4A:
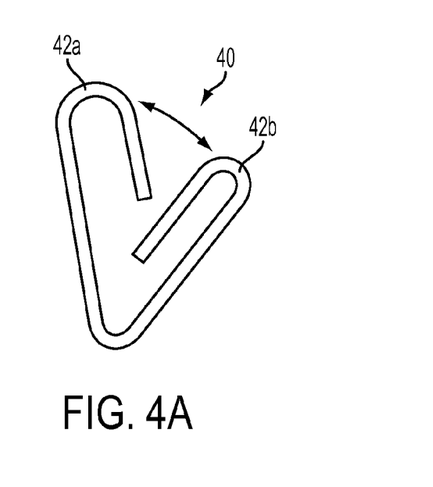
FIG. 4A is a front perspective view of one embodiment of a clip, shown in an open position, and effective to induce ischemic necrosis in tissue surrounding an anastomosis fistula.
Figure 4B:
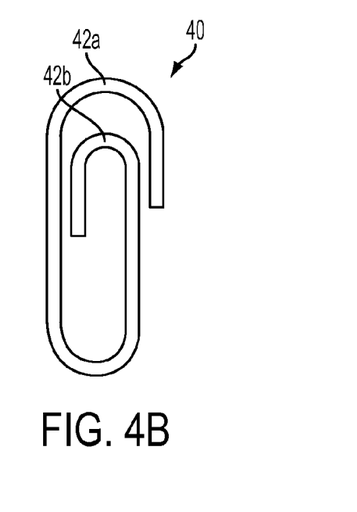
FIG. 4B is a front perspective view of the clip in FIG. 4A, shown in a closed position.

FIG. 4 illustrates another embodiment of a clip 40 that is biased to a closed position. The clip 40 has a design similar to a standard office paperclip. The clip 40 can be formed from a single piece of biocompatible material bent into the shape illustrated in FIG. 4B. In operation, the first and second ends 42a, 42b of the clip could be inserted into a forceps-like delivery device that holds the clip in the open position illustrated in FIG. 4A. When the clip is properly located over the tissue of the anastomosis fistula, the delivery device can eject the clip using, for example, a pushing rod, and the natural bias of the clip 40 will bring it to the closed position illustrated in FIG. 4B, thereby exerting pressure on the tissue located between the first and second ends 42a, 42b of the clip.

Figure 5A:
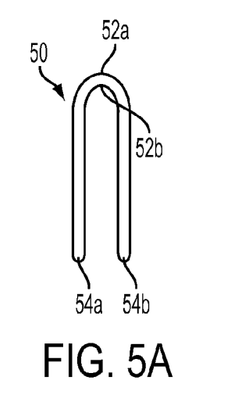
FIG. 5A is a front perspective view of one embodiment of a clip, shown in a constrained position, and effective to induce ischemic necrosis in tissue surrounding an anastomosis fistula.
Figure 5B:
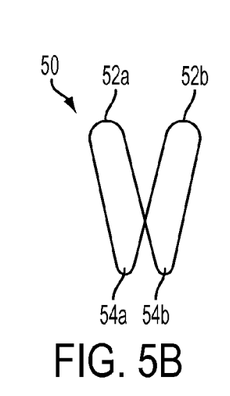
FIG. 5B is a front perspective view of the clip in FIG. 5A, shown in an open position.
Figure 5C:
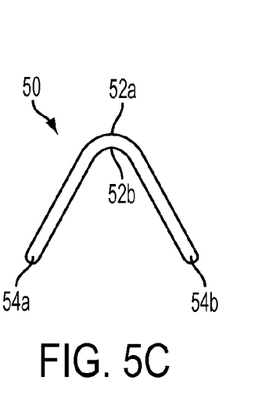
FIG. 5C is a front perspective view of the clip in FIG. 5A, shown in a closed position.

FIG. 5B illustrates still another embodiment of a clip 50 biased to a closed position. The clip 50 can be also formed from a single piece of biocompatible material bent into the shape illustrated in FIG. 5C. In operation, a forceps-like delivery device could hold the clip 50 in the configuration shown in FIG. 5A by constraining the clip's first and second joining bends 54a, 54b to deliver the clip to the anastomosis in a narrow configuration. To position the clip 50 over the tissue of the anastomosis fistula, the delivery device could hold the clip in the position illustrated in FIG. 5B, where the first and second ends 52a, 52b are separated and first and second joining bends 54a, 54b are still constrained. When the clip 50 is properly located, the delivery device can eject the clip using, for example, a pusher rod, and the natural bias of the clip will bring it to the closed position illustrated in FIG. 5C, thereby exerting pressure on the tissue located between the first and second ends 52a, 52b of the clip.

Figures 6A, 6B:
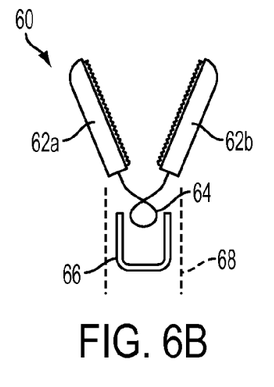
FIG. 6A is a front perspective view of one embodiment of a clip, shown in a constrained position, and effective to induce ischemic necrosis in tissue surrounding an anastomosis fistula.
FIG. 6B is a front perspective view of the clip in FIG. 6A, shown in an open position.
Figure 6C:
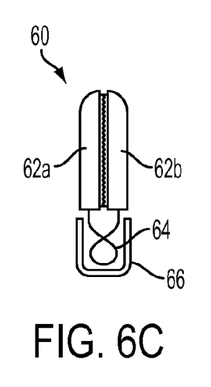
FIG. 6C is a front perspective view of the clip in FIG. 6A, shown in a closed position.

FIG. 6 illustrates another embodiment of a clip 60 that is biased to an open position and depends on a retaining member to supply a closing force. The clip has first and second legs 62a, 62b, spring or other biasing element 64, and retaining member 66. Retaining member 66 can take any form effective to constrain the spring 64 and hold the first and second legs 62a, 62b in the closed position illustrated in FIG. 6C. In operation, clip 60 is carried inside a catheter or endoscope 68 (shown in phantom) such that first and second legs 62a, 62b are constrained in the configuration illustrated in FIG. 6A. In this configuration, the spring 64 is at least partially outside the retaining member 66 and the first and second legs 62a, 62b are primarily constrained by the catheter or endoscope 68. To position the clip 60 over the tissue of an anastomosis fistula, the clip can be partially advanced out of the catheter or endoscope 68 using, for example, a pusher rod. The clip 60 can be advanced such that first and second legs 62a, 62b are no longer constrained by the catheter or endoscope 68 walls and assumes the configuration shown in FIG. 6B. When the clip 60 is properly located, the first and second legs 62a, 62b and spring 64 can be withdrawn into the retaining member 66 by, for example, pulling on the spring 64 with a hook or guidewire. The retaining member 66 will then provide a closing force to secure the first and second legs 62a, 62b in the position illustrated in FIG. 6C. The clip 60 can then be ejected from the catheter or endoscope using, for example, a pusher rod. Alternatively, the catheter or endoscope 68 can have an inner narrowing lumen that prevents the retaining member 66 from retracting as the first and second legs 62a, 62b are pulled back toward the retaining member 66.

Figure 7A:
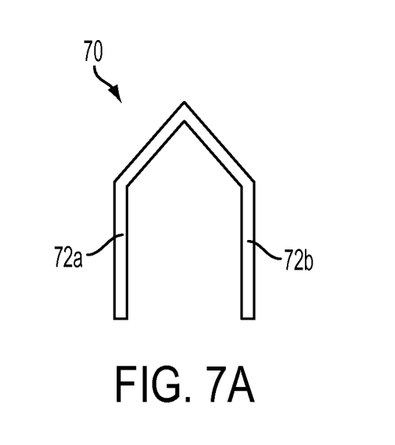
FIG. 7A is a front perspective view of another embodiment of a clip, shown in an open position, and effective to induce ischemic necrosis in tissue surrounding an anastomosis fistula.
Figure 7B:
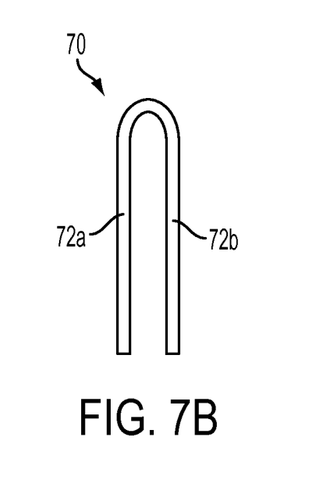
FIG. 7B is a front perspective view of the clip in FIG. 7A, shown in a closed position.

FIG. 7 illustrates another embodiment of a clip 70, which is similar to the LIGAMAX™ clips made by Ethicon Endo-Surgery, Inc. As shown, the clip 70 has first and second legs 72a, 72b that extend generally parallel to one another. The clip is deformable to allow the legs 72a, 72b to be moved from an open position, shown in FIG. 7A, to a closed position, shown in FIG. 7B. The clip can be deformed using various clip applicators or delivery devices known in the art. In general, such devices include a handle and a generally elongate shaft having one or more clips disposed therein. An advancer extends through the shaft for advancing a clip into opposed jaws, and once the jaws are positioned to engage tissue, closure of the jaws is effective to deform the clip into the closed position around the tissue. The deformed clip will exert the necessary pressure on the surrounding tissue.

Figure 8A:
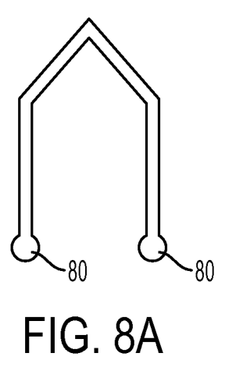
FIG. 8A is a front perspective view of an embodiment of a clip having first and second legs with ball-shaped terminal ends.
Figure 8B:
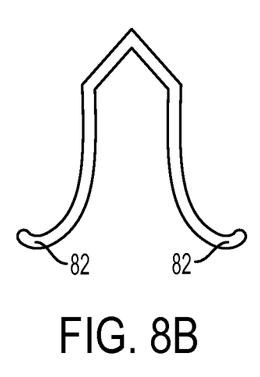
FIG. 8B is a front perspective view of one embodiment of a clip having first and second legs with curled terminal ends.
Figure 8C:
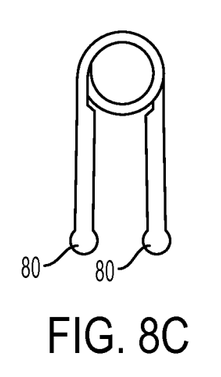
FIG. 8C is a front perspective view of another embodiment of a clip having first and second legs with ball-shaped terminal ends.

The clips used with the present invention can also include features that prevent the terminal ends of the clip from injuring surrounding tissue. Examples of such features include ball-shaped terminal ends 80, as illustrated in FIGS. 8A and 8C, as well as curved terminal ends 82, as illustrated in FIG. 8B. These features can be integrated into any of the embodiments discussed herein, or into any clip known in the art.

In addition, the clips used with the present invention can include features that aid the clips in grasping tissue. For example, the clips can contain features such as serrations on the surface or even small needle-like teeth that aid in grasping tissue. The clip illustrated in FIG. 6 is shown with exemplary needle-like teeth, but one of skill in the art will appreciate that such a feature could be added to any of the clip embodiments discussed herein.

The clip can be delivered using a variety of delivery devices and techniques known in the art. In an exemplary embodiment, the clip is delivered using a flexible device that is capable of traveling endoscopically or laparoscopically to a surgical site, such as through a gastroscope, endoscope, side viewer, or colonoscope. One exemplary delivery device for delivering a clip, such as the clip 30 shown in FIGS. 3A-3B, is described in detail in U.S. Pat. No. 7,357,806, which is hereby incorporated by reference in its entirety. In general, the device is configured to hold a spring-biased clip in an open position, and to release it once properly positioned to allow the clip to return to its closed position. Another exemplary delivery device for delivering a clip, such as the clip 70 shown in FIGS. 7A-7B, is described in detail in U.S. Pat. No. 6,843,794, which is hereby incorporated by reference in its entirety. In general, the delivery device has opposed jaws for holding the clip in an open configuration and for deforming the clip to close it around tissue. In other embodiments, the delivery device can be in the form of a catheter having a pusher rod to advance a clip, such as the clip 60, toward the distal end of the catheter, and a hook and guidewire can pull the first and second legs 62a, 62b of the clip back into the retaining member 66.

Exemplary methods for enlarging an anastomosis fistula are also provided. In general, a clip is delivered through a lumen to the site of a strictured anastomosis formed between the first lumen and a second lumen. The clip can be delivered using a delivery device, which can be inserted endoscopically (e.g., through a natural orifice) or laparoscopically (through an access port) into the lumen. The delivery device can be inserted directly into the lumen, or it can be passed through an endoscope, trocar, or other surgical access device. Once inserted into the lumen, the clip can be positioned such that a first leg is generally positioned in the first lumen and a second leg is generally positioned in the second lumen, i.e., on opposite sites of the anastomosis, with the anastomosis tissue disposed between the legs. The clip can then be released to allow the clip to move to a closed position, or it can be deformed into a closed position. The legs of the clip will apply pressure to the tissue that causes ischemic necrosis in the tissue engaged by the clip. Once necrosis occurs, the dead tissue and clip will slough off from the anastomosis, thereby increasing a diameter of the anastomosis.

Figure 9:
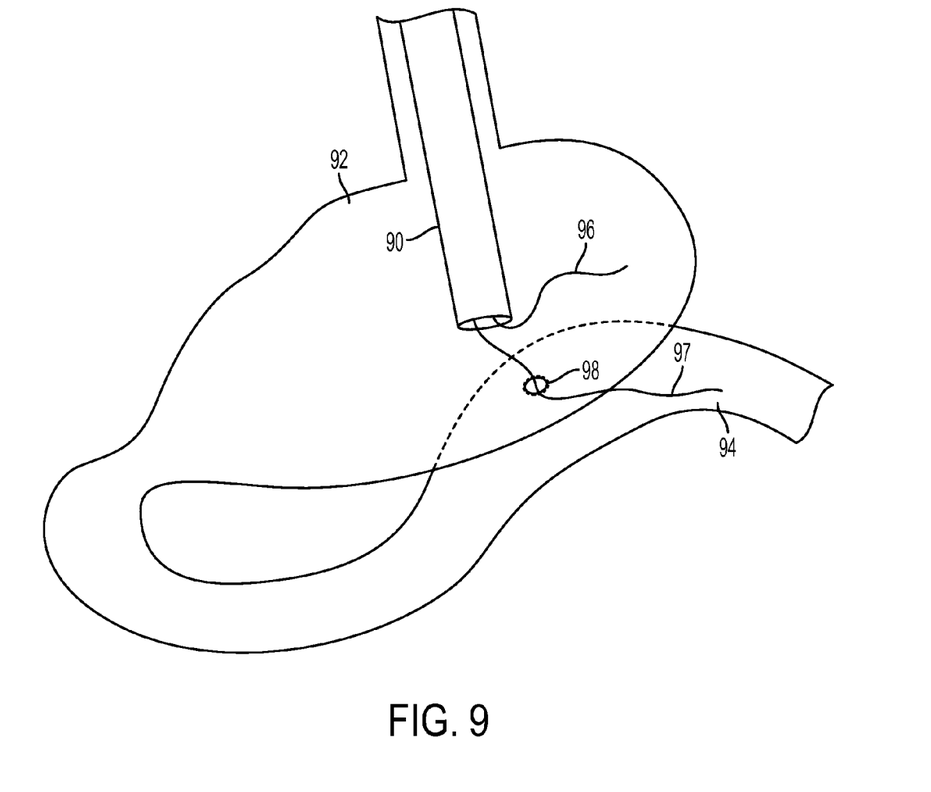
FIG. 9 is a front perspective view of an endoscope and guidewires advanced to the location of a strictured anastomosis fistula.

FIGS. 9-12 illustrate one exemplary method for delivering the clip 30 of FIGS. 3A-3B. As shown, two guidewires 96, 97 can be advanced through an endoscope 90 and into first and second lumens 92, 94, as depicted in FIG. 9. In particular, a terminal end of the first guidewire 96 can be positioned within a first lumen 92, e.g., the stomach, and a terminal end of the second guidewire 97 can be passed through a strictured anastomosis fistula 98 and into the second lumen 94, e.g., the intestine. A viewing element on the endoscope can be used to confirm the position of the guidewires, and/or the position of the guidewires can be checked with fluoroscopy or laparoscopy as is known in the art.

Figure 10:
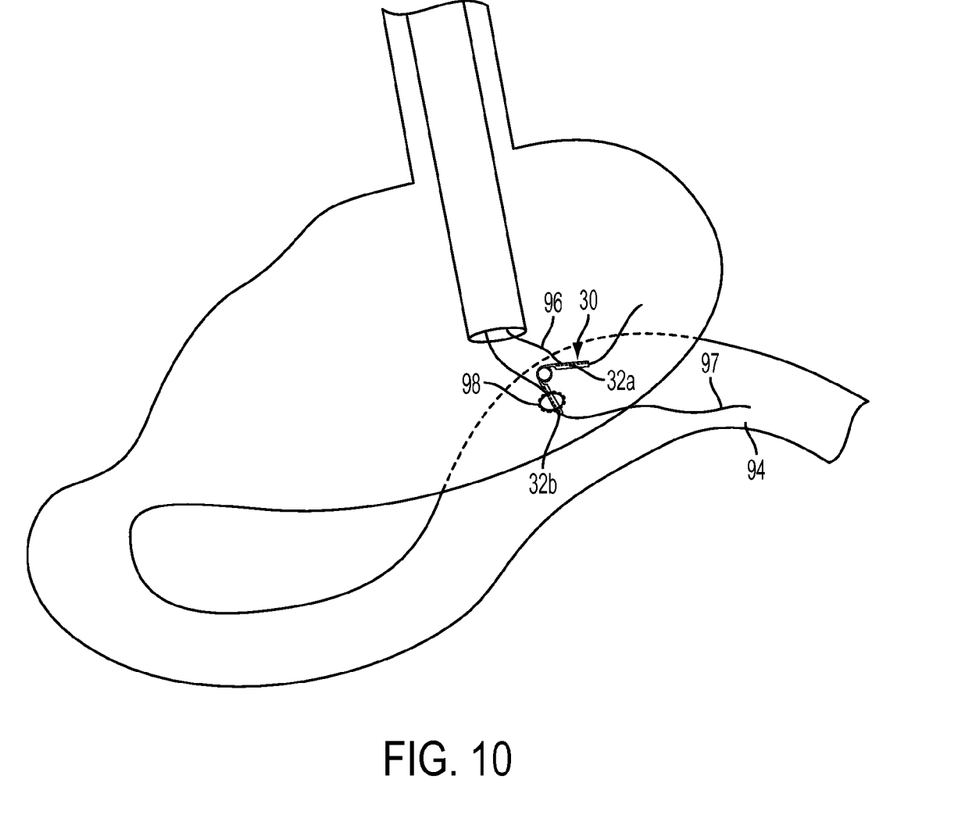
FIG. 10 is a front perspective view of a clip being applied to a strictured anastomosis fistula by advancing the clip along two guidewires.

A clip 30 can be advanced along both of the guidewires 96, 97 through the endoscope 90 to the site of the strictured anastomosis 98. The first and second legs 32a, 32b of the clip, which each have a lumen through which one of the guidewires can be passed, can be split such that the first leg 32a of the clip passes along the first guidewire 96 and is positioned in the first lumen 92, and the second leg 32b of the clip passes along the second guidewire 97, through the strictured anastomosis fistula 98, and is positioned in the second lumen 94, as illustrated in FIG. 10.

Figure 11:
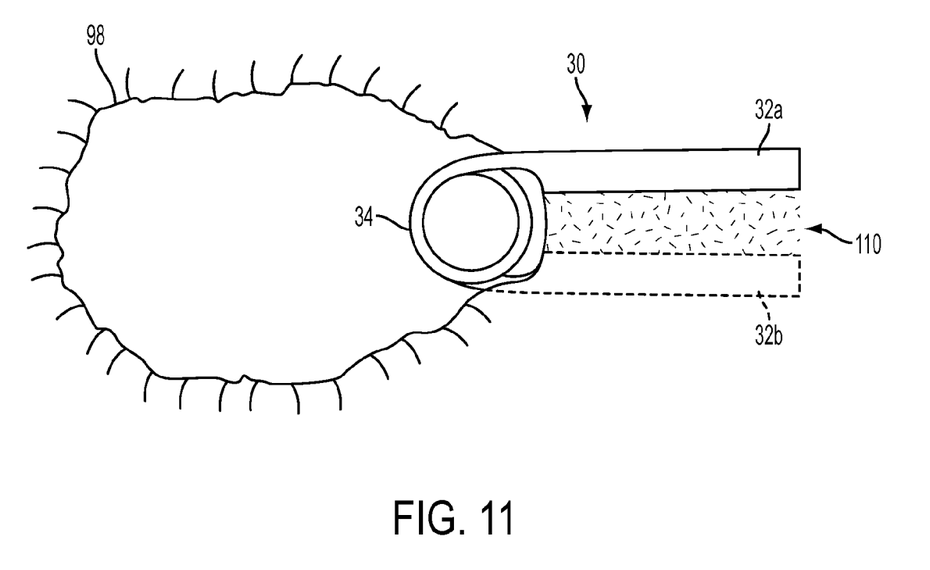
FIG. 11 is a front perspective view of a clip after application to a strictured anastomosis fistula.

Once the clip is correctly positioned around a portion of the tissue surrounding the strictured anastomosis fistula 98, the clip 30 can be released from the delivery device. The biasing mechanism, e.g., spring 34, will cause the legs 32a, 32b to move toward one another into a closed position, thereby applying a compressive force to the tissue 110 disposed between the first and second legs 32a, 32b. The guidewires 96, 97 and endoscope 90 can then be removed from the site, leaving the clip 30 securely attached to the tissue 110 surrounding the strictured anastomosis fistula 98, as depicted in FIG. 11.

Figure 12:
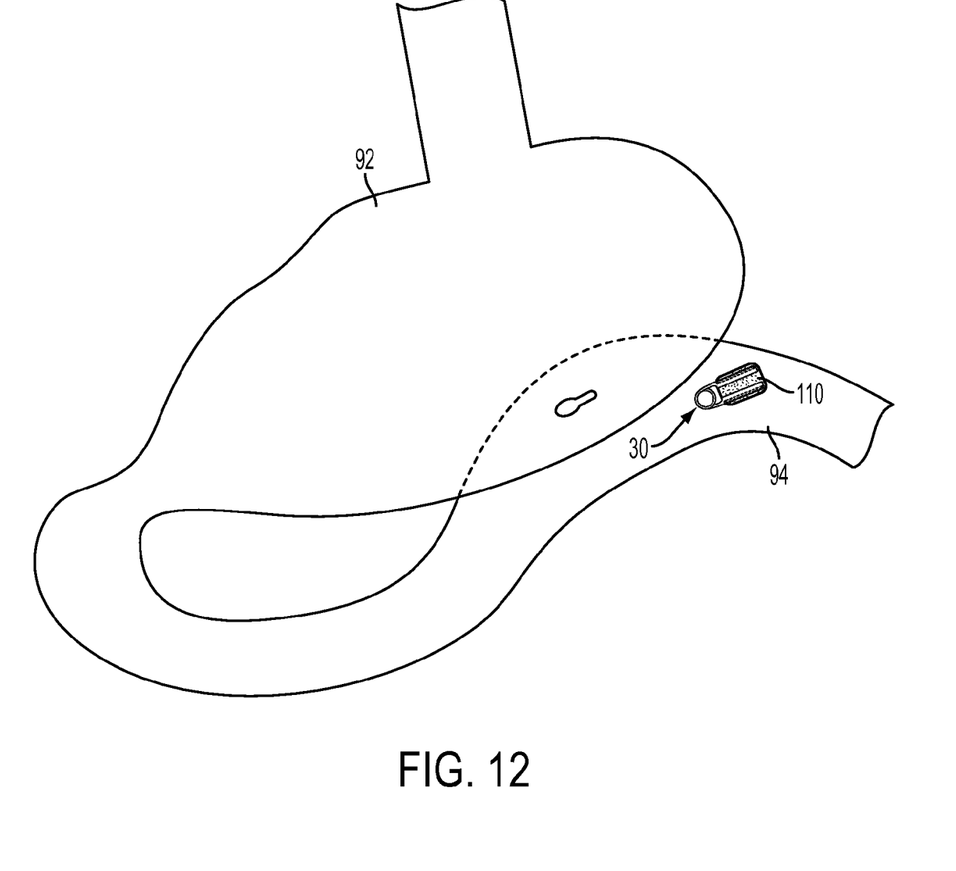
FIG. 12 is a front perspective view of a clip and surrounding tissue sloughing off due to ischemic necrosis.

After a period of time, the pressure applied to the tissue 110 by the clip causes a loss of blood to the tissue, thus inducing necrosis. The stress can also induce a healing response in the immediately surrounding tissue, due to increased blood in the surrounding tissue, thus causing the tissue of the first and second lumens 92, 94 to more completely fuse together. Once necrosis occurs, the dead tissue 110 and clip 30 will slough off from the anastomosis. As shown in FIG. 12, the clip 30 and tissue 110 can pass through the digestive tract. The resulting anastomosis between the first lumen 92, e.g., the stomach, and the second lumen 94, e.g., the small intestine, has a larger inner diameter than the strictured anastomosis and is capable of passing larger masses of gastrointestinal contents between the two spaces.

Figure 13A:
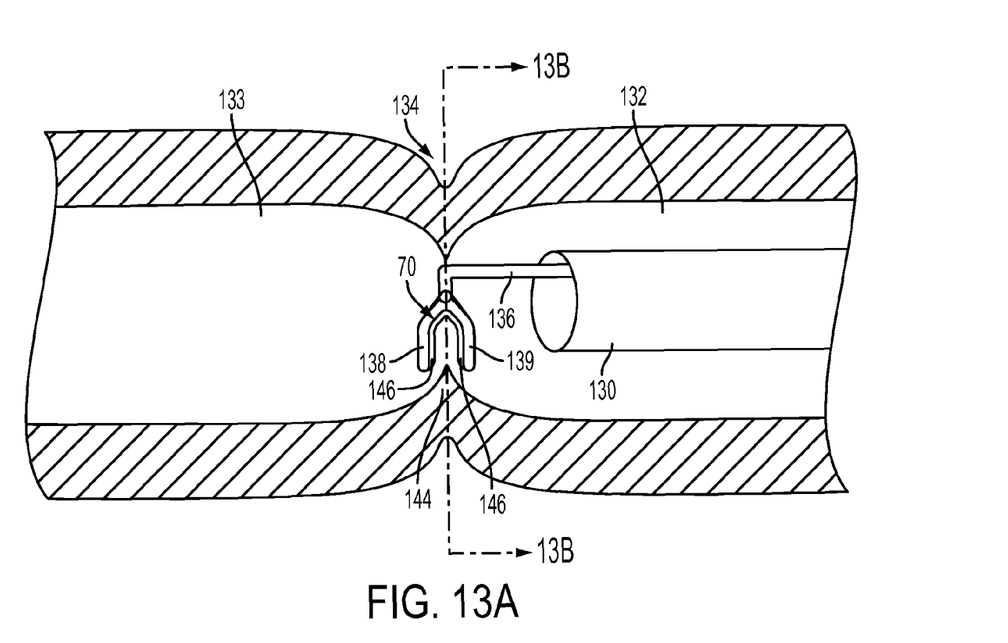
FIG. 13A is a side perspective view of a delivery device positioning a clip over a strictured anastomosis fistula.
Figure 13B:
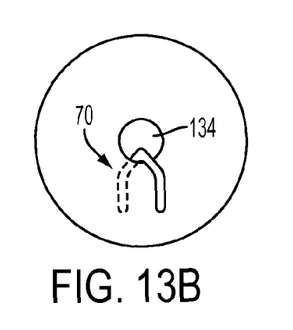
FIG. 13B is a cross-sectional view of the strictured anastomosis of FIG. 13A, shown before application of a clip.

FIGS. 13A-15 illustrate another method for enlarging an anastomosis fistula. As shown in FIG. 13A, an endoscope 130 or similar endoscopic or laparoscopic device is advanced through a first lumen 132 to a site of a strictured anastomosis 134 formed between the first lumen 134 and a second lumen 133. A delivery device 136 can be advanced through the endoscope to the site of the anastomosis fistula. The illustrated delivery device includes forceps having first and second jaws 138, 139 that are configured to receive opposed legs of a clip therebetween, such as legs 72a, 72b of clip 70 shown in FIGS. 7A-7B. The delivery device is used to position the clip 70 such that it can be clamped on to tissue 144 surrounding the strictured anastomosis fistula 134. FIG. 13B illustrates the clip positioned such that opposed terminal ends 146 of the clip 70 are positioned on opposite sides of the anastomosis 134, with the spine or mid-portion of the clip 70 extending therebetween.

Figure 14:
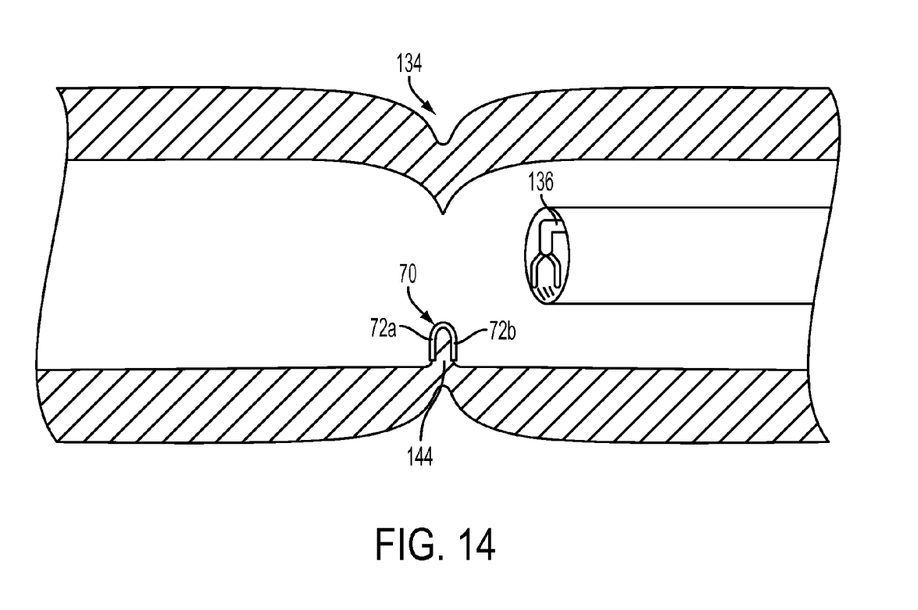
FIG. 14 is a side perspective view of a clip applied to a strictured anastomosis fistula by a delivery device.
Figure 15:
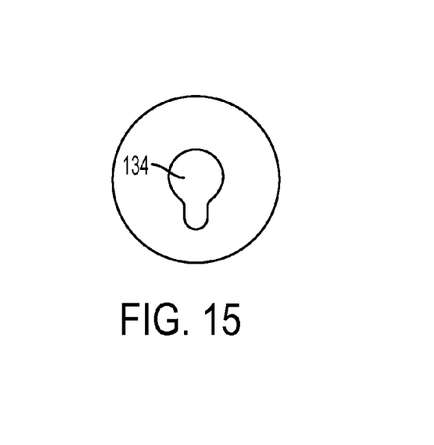
FIG. 15 is a cross-sectional view of an anastomosis, showing an enlarged anastomosis fistula.

Once the clip 70 is properly positioned, the jaws 138, 139 can be closed to deform the clip around the tissue 144 disposed between the first and second legs 72a, 72b. The delivery device 136 can then be removed from the site of the strictured anastomosis 134, as depicted in FIG. 14. The clip 70 will exert a pressure on the tissue after the delivery device 136 is removed. After a period of time, the loss of blood due to the pressure applied by the clip 70 will cause the tissue 144 between the clip legs 72a, 72b to undergo necrosis. The stress also can induce a healing response in the immediately surrounding tissue, as discussed above. Once necrosis occurs, the dead tissue 144 and clip 70 will slough off from the anastomosis 134 and pass through the patient's digestive tract. The resulting anastomosis fistula 134 can have a cross-sectional shape substantially as illustrated in FIG. 15, which is larger than the original strictured anastomosis fistula illustrated in cross section in FIG. 13B.

Figure 16A:
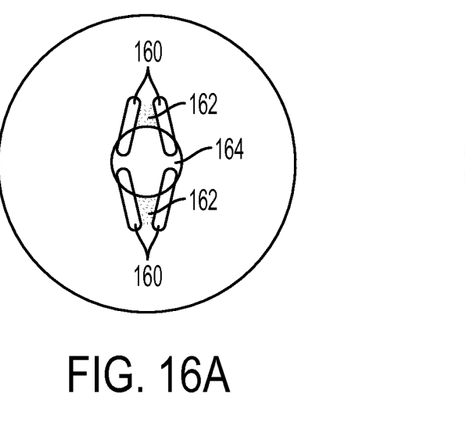
FIG. 16A is front perspective view of a strictured anastomosis, showing the application of multiple clips.
Figure 16B:
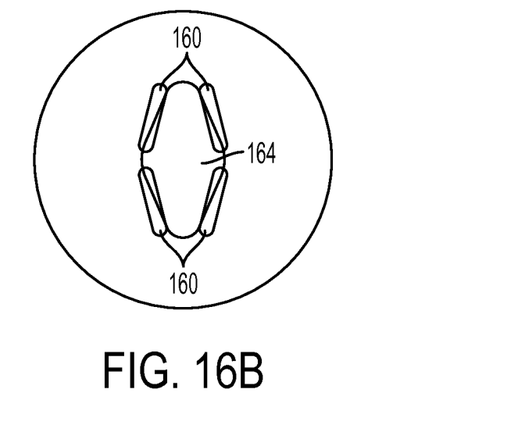
FIG. 16B is a front perspective view of the anastomosis in FIG. 16A, showing immediate fistula expansion from a cutting operation.

All of the methods disclosed herein can be modified in various ways and still be considered within the scope of the invention. For example, multiple clips can be applied to a single anastomosis fistula to provide a greater expansion of the anastomosis diameter. Multiple clips can also be combined with cutting operations to achieve a faster and greater expansion of the anastomosis diameter. An example of such a procedure is illustrated in FIGS. 16A and 16B. First, multiple clips 160 can be applied to a strictured anastomosis 164 using any of the methods described above. The clips can be positioned to create patches of tissue 162 that are supported between the clips 160, as shown in FIG. 16A. Scissors, needle-knives, or radio-frequency cutters can then be used to remove the patches of tissue 162, leaving an anastomosis 164 like that illustrated in FIG. 16B. The cutting operation provides some expansion of the anastomosis fistula instantly, and further expansion after the clips 160 slough off with the necrosed tissue. In cases where radio-frequency cutting is used, the clips 160 should preferably be formed of an electrically inert material to avoid cauterizing the tissue held by the clips.

The present invention can also be used at other anatomical sites. For example, one or more clips can be used to remove tissue (through necrosis) to increase blood flow at anatomical sites such as Zenker's pharyngeal diverticulae, or for use in pyloroplasties, biliary sphincterotomies, and also for dealing with pathological strictures such as esophageal webs, small intestinal webs, and short colonic strictures.

As another example, the clips of the present invention can be fitted with a passive Radio Frequency Identification (RFID) tag that can be swiped with a detector to determine the general location of the clip. In particular, this feature can be used to confirm that the clip has passed out of a patient's body without the need for X-rays or further endoscopy.

As will be appreciated by those skilled in the art, any and all of the embodiments disclosed herein can be interchangeable with one another as needed. For example, a delivery device may be utilized in the embodiment depicted in FIGS. 9-12, or the blunt terminal end features illustrated in FIGS. 8A-8C may be added to any of the clips discussed herein.

One skilled in the art will appreciate further features and advantages of the invention based on the above-described embodiments. Accordingly, the invention is not to be limited by what has been particularly shown and described, except as indicated by the appended claims.

What is claimed is:

1. A method of enlarging an anastomosis fistula, comprising:
    advancing an endoscope through a first lumen to a site of a strictured anastomosis formed between the first lumen and a second lumen; and
    positioning a first leg of a clip in the second lumen and positioning a second leg of the clip in the first lumen;
    wherein the first and second legs of the clip are closed to apply a pressure to tissue surrounding the strictured anastomosis, the pressure being sufficient to induce ischemic necrosis in the compressed tissue.

2. The method of claim 1, further comprising, prior to positioning, advancing the clip along at least one guidewire.

3. The method of claim 1, further comprising, prior to positioning, advancing the first leg of the clip along a first guidewire extending through the endoscope, and advancing the second leg of the clip along a second guidewire extending through the endoscope.

4. The method of claim 1, further comprising, prior to positioning, passing a first guidewire through the endoscope and the strictured anastomosis to position a distal end of the first guidewire in the second lumen, passing a second guidewire through the endoscope to position a distal end of the second guidewire in the first lumen, and advancing the first leg of the clip along the first guidewire and advancing the second leg of the clip along the second guidewire.

5. The method of claim 1, wherein the first and second legs of the clip are biased to a closed position, and wherein the first and second legs of the clip are closed by releasing the clip from a delivery device.

6. The method of claim 1, wherein the first and second legs of the clip have ball-shaped ends to prevent puncturing the lumen walls.

7. The method of claim 1, wherein the first and second legs of the clip have curled ends to prevent puncturing the lumen walls.

8. The method of claim 1, wherein the first lumen is the stomach and the second lumen is the small intestine.

9. The method of claim 1, further comprising, prior to positioning the clip, advancing a flexible clip applier through the endoscope to position the clip adjacent to the strictured anastomosis.

10. The method of claim 1, wherein the first and second legs of the clip are closed by deforming the shape of the legs with a delivery device.

11. A method for enlarging an anastomosis fistula, comprising:
    advancing an endoscope through a first body lumen to position a distal end of the endoscope adjacent to a strictured anastomosis formed between the first body lumen and a second body lumen;
    applying a clip to the strictured anastomosis such that first and second terminal ends of the clip apply a pressure sufficient to induce ischemic necrosis to cause the clip and surrounding tissue to slough off and thereby increase a diameter of the anastomosis fistula.

12. The method of claim 11, wherein the first and second terminal ends of the clip are positioned on opposed sides of the anastomosis.

13. The method of claim 11, further comprising, prior to applying the clip, advancing the clip along at least one guidewire.

14. The method of claim 11, further comprising, prior to applying the clip, advancing the first terminal end of the clip along a first guidewire extending through the endoscope, and advancing the second terminal end of the clip along a second guidewire extending through the endoscope.

15. The method of claim 11, further comprising, prior to applying the clip, passing a first guidewire through the endoscope and the strictured anastomosis to position a distal end of the first guidewire in the second lumen, passing a second guidewire through the endoscope to position a distal end of the second guidewire in the first lumen, and advancing the first terminal end of the clip along the first guidewire and advancing the second terminal end of the clip along the second guidewire.

16. The method of claim 11, wherein the terminal ends of the clip are biased to a closed position, and wherein the terminal ends of the clip are closed by releasing the clip from a delivery device.

17. The method of claim 11, wherein the terminal ends of the clip have ball-shaped ends to prevent puncturing the lumen walls.

18. The method of claim 11, wherein the terminal ends of the clip have curled ends to prevent puncturing the lumen walls.

19. The method of claim 11, wherein the first lumen is the stomach and the second lumen is the small intestine.

20. The method of claim 11, further comprising, prior to applying the clip, advancing a flexible clip applier through the endoscope to position the clip adjacent to the strictured anastomosis.

\* \* \* \* \*